(12) United States Patent
Diaz et al.

(10) Patent No.: US 10,111,612 B2
(45) Date of Patent: Oct. 30, 2018

(54) VIRTUAL MAGNETIC TRANSMISSION LINES FOR COMMUNICATION AND POWER TRANSFER IN CONDUCTING MEDIA

(71) Applicant: Arizona Board of Regents on behalf of Arizona State University, Scottsdale, AZ (US)

(72) Inventors: Rodolfo E. Diaz, Phoenix, AZ (US); Tara Yousefi, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/551,118

(22) PCT Filed: Feb. 18, 2016

(86) PCT No.: PCT/US2016/018400
§ 371 (c)(1),
(2) Date: Aug. 15, 2017

(87) PCT Pub. No.: WO2016/134107
PCT Pub. Date: Aug. 25, 2016

(65) Prior Publication Data
US 2018/0069439 A1 Mar. 8, 2018

Related U.S. Application Data

(60) Provisional application No. 62/118,339, filed on Feb. 19, 2015.

(51) Int. Cl.
*A61B 5/00* (2006.01)
*H02J 50/23* (2016.01)
(Continued)

(52) U.S. Cl.
CPC ............ *A61B 5/40* (2013.01); *H02J 50/12* (2016.02); *H02J 50/23* (2016.02); *H04B 5/0037* (2013.01); *H01F 2038/143* (2013.01)

(58) Field of Classification Search
CPC . H02J 50/10; H02J 50/12; H02J 50/23; A61B 5/0002–5/0031
See application file for complete search history.

(56) References Cited

U.S. PATENT DOCUMENTS 4,361,153 A * 11/1982 Slocum ............... A61B 5/0017
128/903
6,233,490 B1 * 5/2001 Kasevich ............... A61B 18/18
606/33

(Continued)

OTHER PUBLICATIONS

Krasnok et al., "All-dielectric optical nanoantennas", Aug. 27, 2012, Optics Express, p. 20599-20604.*

(Continued)

*Primary Examiner* — Dean Takaoka
*Assistant Examiner* — Alan Wong
(74) *Attorney, Agent, or Firm* — Yakov S. Sidorin; Quarles & Brady LLP

(57) ABSTRACT

System and method for wireless, low-loss transmission in conductive medium of a radio-frequency signal received by a passive array of magnetic dipole elements from a source magnetic dipole. The individual elements are separated from one another by a distance on the order of or less than a quarter-wavelength corresponding to resonant radio-frequency. An array individual elements of which are microscopically dimensioned form a neuronal transmitter that can be configured to be implanted into neuronal tissue such that a source dipole, disposed near a neuron, passes a signal representative of neuronal activity along the array to an outmost element and further to external receiver disposed (Continued)

Size of antennas exaggerated for clarity near skull. Macroscopically-dimensioned embodiment is configured to be submerged into and operate in salty water.

6 Claims, 8 Drawing Sheets

(51) Int. Cl.
*H04B 5/00* (2006.01)
*H02J 50/12* (2016.01)
*H01F 38/14* (2006.01)

(56) References Cited

U.S. PATENT DOCUMENTS

| | | | | |
|---|---|---|---|---|
| 7,357,037 | B2 * | 4/2008 | Hnat | A61B 5/0031 73/795 |
| 7,535,364 | B2 * | 5/2009 | Sakama | G06K 7/10178 340/572.1 |
| 7,840,250 | B2 * | 11/2010 | Tucker | A61B 5/04 600/407 |
| 8,144,070 | B2 * | 3/2012 | Wright | H01Q 1/08 343/815 |
| 8,634,928 | B1 | 1/2014 | O'Driscoll et al. | |
| 9,418,785 | B2 * | 8/2016 | Park | H01F 38/14 |
| 2009/0102590 | A1 * | 4/2009 | Rhodes | H01F 38/14 336/107 |
| 2011/0074349 | A1 | 3/2011 | Ghovanloo | |
| 2011/0156492 | A1 | 6/2011 | Ryu et al. | |
| 2014/0246924 | A1 | 9/2014 | Proud | |
| 2015/0080637 | A1 * | 3/2015 | Bonmassar | A61N 2/006 600/14 |
| 2017/0319096 | A1 * | 11/2017 | Kaiser | A61B 5/0031 |

OTHER PUBLICATIONS

Floc'h et al, "Design of Printed Dipole Antenna with Reflector and Multi-Directors", Jun. 2010, IRECAP, 8 pages.*
Liu et al., "Microstrip Magnetic Dipole Yagi Array Antenna With Endfire Radiation and Vertical Polarization", Mar. 2013, IEEE Transactions on Antennas and Progagation, vol. 61, No. 3, pp. 1140-1147.*
Yang et al., "Wideband microstrip series-fed magnetic dipole array antenna", Nov. 20, 2014, Electronics Letters vol. 50, No. 24, pp. 1793-1795.*
The International Search Report and Written Opinion for International Patent Application No. PCT/US2016/018400 dated May 20, 2016.
R. E. Diaz et al., Electromagnetic limits to radiofrequency (RF) neuronal telemetry, Scientific Reports 3, Dec. 18, 2013, Article No. 3535; DOI:10.1038/srep03535 (2013).

* cited by examiner

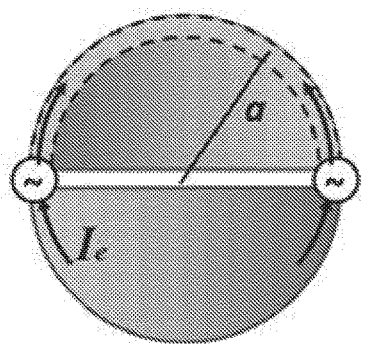
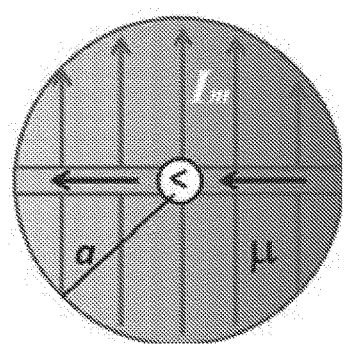

FIG. 4A    FIG. 4B

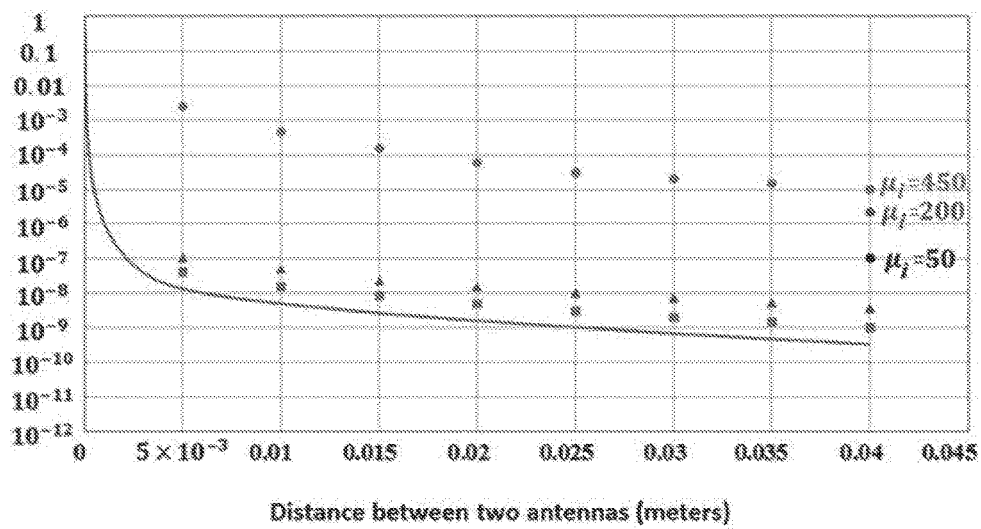

Distance between two antennas (meters)

— Field ratio [ $E_\theta(r)/E_\theta(a)$ of the electric dipole and $H_\phi(r)/H_\phi(a)$ of the magnetic dipole and $H_\phi(r)/H_\phi(a)$ of the electric loop] which is the ratio of the field at that point normalized to the field at the surface of the source and whether we plot this for the electric dipole, electric loop, or magnetic dipole the results exactly overlay and are indiscernible from each other.

◆ Magnetic dipole current ratio
▲ Electric loop current ratio
▇ Electric dipole current ratio

FIG. 5

Size of antennas exaggerated for clarity

VIRTUAL MAGNETIC TRANSMISSION LINES FOR COMMUNICATION AND POWER TRANSFER IN CONDUCTING MEDIA

CROSS-REFERENCE TO RELATED APPLICATIONS

This patent application represents the national stage entry of a PCT International Application No. PCT/US2016/018400 filed on Feb 18, 2016 and claims priority from and benefit of the U.S. Provisional Patent Application No. 62/118,339 filed on Feb. 19, 2015. The disclosure of each of the above-mentioned applications is incorporated herein by reference.

TECHNICAL FIELD

The present invention relates to systems and method for wireless transmission in the radiofrequency range and, in particular, to arrays of passive antenna elements operating substantially losslessly in the conductive fluid environment.

SUMMARY

Embodiments of the invention provide a wireless power transmission line that includes a source magnetic dipole element configured to operate at a chosen frequency; and an array of magnetic dipole elements separated from one another by a distance defining near-field interaction between immediately neighboring magnetic dipole element from said array, an outmost element of said array separated from said source by said distance. The transmission line is configured to operate in a conductive medium.

Embodiments further include a method for wireless transmission of power in a conductive environment. The method contains steps of (i) causing a source magnetic dipole element radiate energy by emitting a signal at a chosen frequency; (ii) passively transferring the signal between the source magnetic dipole element and an outer element at a first end of an array of magnetic dipole elements, which outer element is separated from the source magnetic dipole element by a distance defining a near-field interaction; and (iii) passively transferring the signal from the outer element to an element at a second end of the array only via near-field interactions between elements of the array.

Embodiments additionally provide a neuronal radio-frequency (RF) telemetry system that includes a microscopically-sized neuronal sensor tuned to a resonance at a chosen radio-frequency; an electronic circuitry operably connected to the neuronal sensor; a passive array of microscopically-sized neuronal transmitter elements separated from one another by a distance defining near-field interaction between immediately neighboring transmitter element from the array, while an outmost transmitter element of the array is separated from the sensor by such by said distance, and a receiver in RF communication at least with the outmost transmitter element

BRIEF DESCRIPTION OF THE DRAWINGS

The invention will be more fully understood by referring to the following Detailed Description of Specific Embodiments in conjunction with the generally not-to-scale Drawings, of which:

FIGS. 4A, 4B illustrate idealized electric-dipole and magnetic dipole antennae.

FIG. 5 is a plot of data representative of the normalized fields of the electric dipole antenna, a magnetic dipole antenna, and an electric loop antenna.

DETAILED DESCRIPTION

Embodiments of the invention solve problems of high-level dissipation of energy (accompanying the operation of a conventional metal (or dielectric) antenna at radio frequencies) in a conducting fluid medium surrounding the antenna and/or into the material of the antenna itself by forming an antenna from physically disconnected but mutually-coupled resonant magnetic dipoles (as opposed to electric dipoles) to allow the energy to spread along the full length of the antenna.

From the impedance point of view, electric loops and electric dipoles are the two fundamental types of antennas. According to Schelkunoff (Antenna Theory and Practice, John Wiley & Sons, 1952), in order to calculate the impedance of an antenna one has to solve Maxwell's equation subject to the specific boundary conditions of the antenna. Notwithstanding, one can obtain some of the important general properties of the impedance from much more basic considerations. These properties are not limited to antennas or electrical systems. They are common to all dynamic systems (for example mechanical and acoustical) and they don't even depend on the form of the dynamical equations as long as those equations are linear. A brief consideration of these general properties of impedance will help to understand the reason of the difference in the antennas behaviors.

For any transmitting antenna the voltage and current at the input terminals can be written as a function of a complex variable which can be called "p" where $p=j\omega$ and $\omega$ is the frequency of oscillation. The ratio of the functions $V(p)$ and $I(p)$ is called the input impedance $Z(p)$ of the antenna and the inverse is called the input admittance $Y(p)$.

Figure 1:
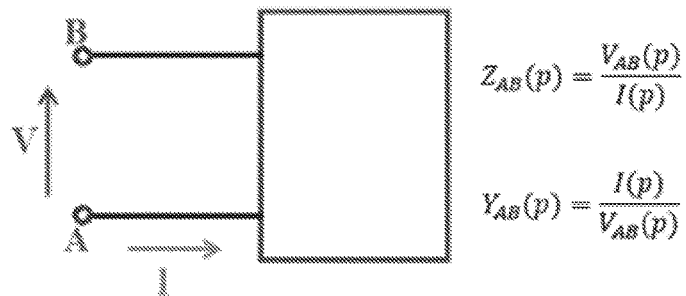
FIG. 1 is a diagram illustrating a network with two accessible terminals.

The schematic in FIG. 1 shows a network with two accessible terminals and in order to introduce the two fundamental antenna types we can write the impedance and admittance as stated in the figure without being interested in their interior structure. The roots of the equation $Z(p)=0$ are called the zeros of the input impedance which are the case for which the voltage across the input impedance vanishes while the current does not. The poles of the impedance are the zeros of the admittance and are roots of the equation $Y(p)=0$ and it is obvious that in this case the input current goes to zero while the voltage does not which means that the terminals of the antenna are floating or the antenna is an open circuit.

Figure 2A:
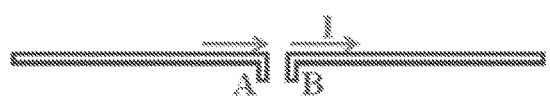
FIGS. 2A, 2B show diagrams illustrating a dipole antenna and a loop antenna.
Figure 2B:
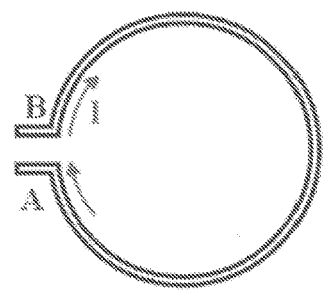

If the terminals of an antenna are open circuited conductors, opposite charges can be placed on these conductors to create a voltage across the input impedance and the current will be zero therefore having $p=0$ as a pole of its input impedance. Such antenna is referred to as a dipole antenna. On the other hand, an antenna consisting of a single perfect conductor having a steady current flowing in it would not have loss. Such antenna is referred to as electric loops and $p=0$ is a zero of the impedance of a perfectly conducting electric loop. FIGS. 2A, 2B show the electric dipole and the electric loop as the two general types of antennas.

This fundamental difference between electric dipole antennas and electric loop antennas is carried through to the case of realistic imperfect environments and materials. The open circuit nature of an electric dipole immersed in a lossy conducting dielectric means that the large voltage developed between its opposite terminals drives a current directly in the medium surrounding it, following the field lines of its near electric field and depositing power into the medium. The short-circuit nature of the electric loop means that it cannot drive a current directly in the surrounding medium. Instead currents are induced via electromagnetic induction of eddy currents by its magnetic near field. As shown in by Diaz, R. E. and Sebastian, T. (Electromagnetic limits to radiofrequency (RF) neuronal telemetry, *Nature Scientific Reports*, SREP-13-03863-T.3d, 2013, the disclosure of which is incorporated herein by reference), for example, this results in the loop dissipating much less power into the surrounding medium; but the fact that metal (such as copper, for example) is not a perfect conductor means that the current in the electric loop will cause it to heat up and dissipate power into its own materials. The disclosure of the above-identified publication is incorporated herein by reference in its entirety.

In other words, a metal loop antenna fares better than a dipole antenna because the metal loop antenna acts as a magnetic dipole and dissipates less heat into the medium through its near field. At the same time, however, the loop antenna is less efficient than the dipole antenna and, therefore, to attain a desired far-field power such loop antenna must carry large current and, therefore, dissipate a large amount of power through internal ohmic losses in the antenna's materials.

A small conventional metal (or dielectric) antenna operating in a conducting fluid medium is known to have a sufficient drawback stemming from the fact that in such conditions the antenna dissipates, in its near-field, several orders of magnitude more power into the conducting fluid that it radiates to the far field. Specifically, for micron-sized antennae at radiofrequencies the root of the problem is the fact that such antennae store orders of magnitude more energy per cycle in their near field than the power they can radiate to the far field. This ratio is known as the Quality factor of the antenna and according to the Fano-Chu limit it is at least of the order of $Q \approx 1/(ka)^3$, where k is a propagation constant of the RF wave in the medium and a is a radius of the smallest sphere into which the antenna at hand can dimensionally fit. For a 20 micron antenna, for example, in the body dielectric at 2 GHz this ratio is of the order of 40 million; for an 80 micron antenna it is of the order of 600,000. Since all realistic materials are lossy, the enormous amount of energy available per cycle in the near field ends up being consumed as heat.

The operational problems discussed above raise the question of whether there is another kind of antenna that can combine the best features of the dipole antenna and the loop antenna, one the near field of which is dominated by a magnetic field and yet does not behave as a short circuit to draw large currents.

Since the above-mentioned problems are related to the operation of an isolated antenna communicating with the outside world by direct radiation of its signal, the embodiments of the present invention solve these problems by configuring the antenna system from a chain of physically disconnected but mutually coupled resonant magnetic dipoles—as opposed to electric dipoles of related art—thereby minimizing the dissipation of energy into the surrounding dielectric medium and allowing the energy to spread along the full length of the antenna system to attain high radiation efficiency. Specifically, the idea of the present invention stems from the realization that an antenna constructed of magnetically-permeable material(s) can be used as a true magnetic dipole radiating with the use of true magnetic current. Consequently, such antenna possesses the low-loss operational properties of the loop antennae in the near-field and the high efficiency operating properties of the dipole antennae in the far-field.

Figure 3A:
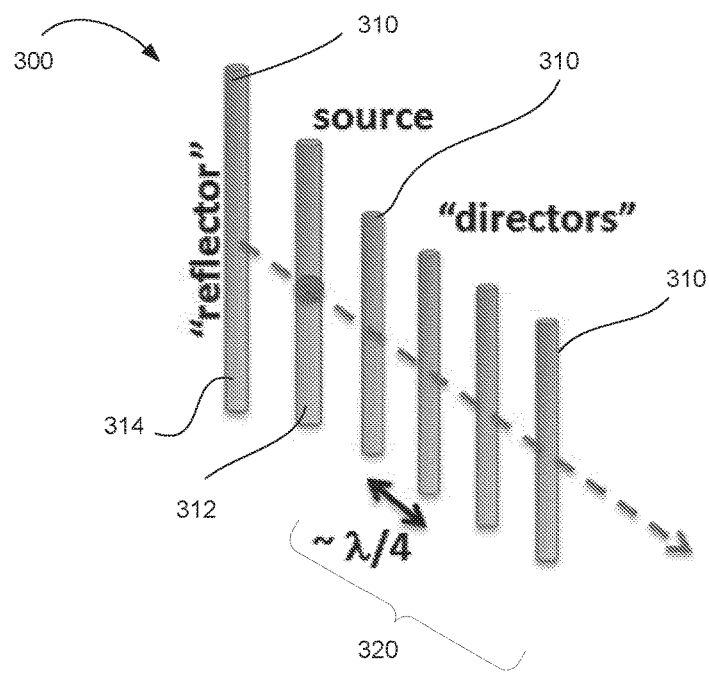
FIG. 3A is a diagram illustrating schematically a transmission line configured according to an embodiment of the invention from permeable true magnetic dipoles in a surrounding medium that has low impedance and/or conductivity (not metallic elements in free space) that are used as elements of an array structured similarly to aYagi-Uda array (that is, in contradistinction with the present embodiment, made of metallic elements in free space).
Figure 3B:
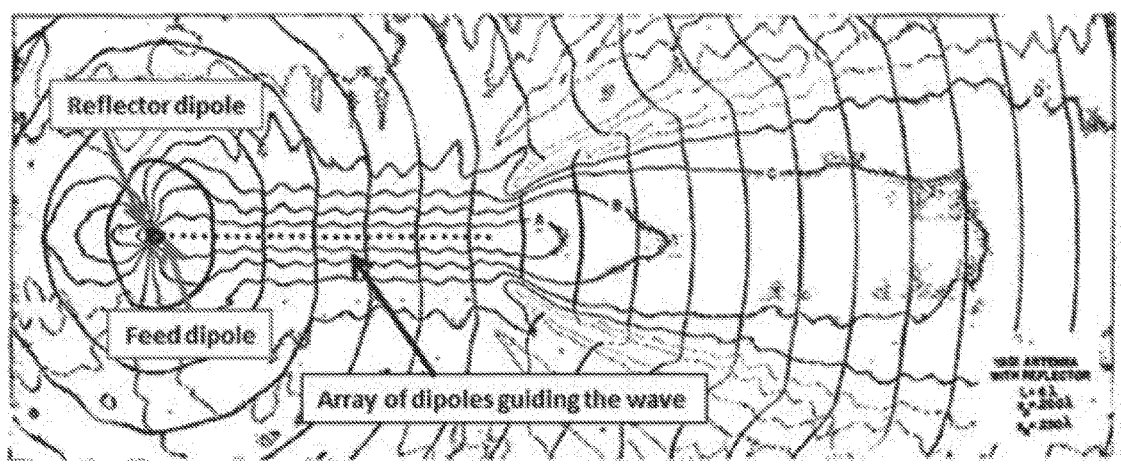
FIG. 3B is a schematic illustration of an RF-wave guidance from a source element along a chain of elements in free space by a Yagi-Uda antenna array of related art.

According to the idea of the invention, and in reference to FIG. 3A, the antenna system 300 (interchangeably referred to herein as a virtual transmission line) is structured as a spatially-reconfigurable chain of individual true magnetic dipoles 310 (each made of a magnetically-permeable material), the immediately adjacent neighboring of which are disposed within the near field of one another (at a distance of about or less then a quarter wavelength) such as to transmit power wirelessly (contactlessly) through the low-loss near field of the chain elements even in the presence of conducting environment (such as the use undersea or while embedded in a biological tissue, for example). In other words, the antenna system is configured from the magnetically-permeable material(s) not to radiate the energy outwards but simply to guide it from one element of the system to another, along the array 320 of the elements 310. In contradistinction, the related-art embodiment of the Yagi-Uda array made of metallic elements radiates the energy outwards, as shown schematically in FIG. 3B.

It is notable that the physical (operational) loss of one or several antenna-elements in the chain does not render the chain inoperable, because such loss is obviated by re-routing the power signal through the near-field of adjacent antenna elements. The spatial structure of the chain of the individual antenna-elements defines the gain and directivity properties of the antenna system.

True Magnetic Dipole

Although in the conventional practice of Antenna Theory and Design a distinction is made between electric dipole antennae (generally metal rods carrying an alternating electric current) and magnetic dipole antennae (generally metal loops carrying an alternating electric current,) in reality both of these antennae types are electric current radiators. In the first type, the electric current is linear and couples most efficiently to the electric dipole modes of the spherical mode spectrum; in the second type, the electric current is circumferential and couples most effectively to the magnetic dipole modes of the spherical mode spectrum.

Most antenna practitioners assume that the absence in nature of observed magnetic monopoles precludes the existence of true magnetic currents and therefore whenever the term "magnetic dipole" is used in related art, a loop antenna is meant, and whenever the term "magnetic current" is used, a fictitious magnetic current is meant. The latter arises in Schelkunoff's Equivalence Theorem whenever it is desired to summarize all the sources on one side of a closed mathematical surface by using the tangential electromagnetic fields existing on that surface. Thus the surface fictitious magnetic current, Km (measured in Volts/meter) is defined as the cross product of the surface normal and the tangential Electric field on that surface.

Embodiments of the present invention utilize true (as opposed to fictitious) magnetic current radiators. That is, in the same way that electric current density, $J_e$, (measured in $A/m^2$) flows through a medium with electric conductivity, $\vec{J}_e$ (measured in Siemens/meter, as $\vec{J}_e = \sigma_e \vec{E}$,), magnetic current density, $J_m$, (measured in $V/m^2$) flows through a medium with magnetic conductivity, $J_m$, (measured in Ohms/meter, as $\vec{J}_e = \sigma_m \vec{E}$,).

Even though magnetic conductivity does not exist at zero frequency (because of the absence of magnetic monopoles), as far as Maxwell's equations are concerned, it exists at any frequency in which a material exhibits a magnetic loss tangent. This is because the imaginary part of the complex permittivity and complex permeability of materials, $$\varepsilon(\omega) = \varepsilon_0(\varepsilon' - j\varepsilon''), \text{ and } \mu(\omega) = \mu_0(\mu' - j\mu''), \tag{1A}$$

imply the existence of a corresponding conductivity through the relations:

$$\sigma_e = \omega \varepsilon_0 \varepsilon'' \tag{1A}$$

$$\sigma_m = \omega \mu_0 \mu'' \tag{1B}$$

Therefore, in Maxwell's curl equations the terms involving the rate of change of the flux densities imply the existence of magnetic currents as well as electric currents, as shown in Eqs. (2A), (2B):

$$j\omega D = j\omega \varepsilon(\omega) E = j\omega \varepsilon_0(\varepsilon' - j\varepsilon'') E = j\omega \varepsilon_0 \varepsilon' E + \omega \varepsilon_0 \varepsilon'' E = j\omega \varepsilon_0 \varepsilon' E + \sigma_e E = j\omega \varepsilon_0 \varepsilon' E + J_e \tag{2A}$$

$$j\omega B = j\omega \mu(\omega) H = j\omega \mu_0(\mu' - j\mu'') H = j\omega \mu_0 \mu' H + \omega \mu_0 \mu'' H = j\omega \mu_0 \mu' H + \sigma_m H = j\omega \mu_0 \mu' H + J_m \tag{2B}$$

Whenever a lossy permeable material is used to carry alternating magnetic field, it behaves exactly as if it were carrying a magnetic current measured in Volts (whereas electric current is measured in Amps.)

As used herein, the term "electric loop" refers to a metal loop with no core, "electric dipole" refers to a copper sphere model of a linear conventional electric dipole, and the true magnetic antennae or true magnetic dipoles are referred to as "magnetic dipoles". The terms "true magnetic dipole" and "magnetic dipole" as used herein refer to and designate a magnetic dipole radiating through an oscillating magnetic polarization in a permeable material. In particular, the terms "true magnetic dipole" and "magnetic dipole" refer to (i) an antenna constructed from high complex permeability materials (e.g. DC permeability>30 and preferably greater than 100), with no particular restriction on the ratio of real to imaginary part of the permeability at any give frequency, which antenna radiates predominantly through the magnetic current density (dB/dt) flowing inside the permeable material. These terms as used do not refer to or encompass loop antennae even though a metallic loop may be used to drive (feed) the magnetic current in the magnetic dipole.

Idealized Antenna Models and Microscopic Implementations Thereof

In the following disclosure, antenna elements sized to operate inside the brain are described as an example, assumed to be spherical with 10 µm in radius. FIGS. 4A, 4B provide schematic diagrams of the idealized antenna models represented by these dipoles. Spherical geometry is chosen for convenience and simplicity of calculations.

The electric dipole can be imagined as a hollow sphere cut in half and fed by a distributed electric voltage source, $V_E$, at the equator such that the total electric current flowing depends on the self-impedance of the antenna (measured in Ohms) according to Eq. (3):

$$I_E = \frac{V_E}{Z_{E\,self}}; \text{ current moment} = I_E \sqrt{\frac{8}{3}} a \tag{3}$$

The magnetic dipole can be imagined as a solid permeable sphere with a conducting belt around its equator, said belt fed by a current source. The current flowing through the belt in Amps is the magnetic Voltage, $V_M$, and the total magnetic current flowing depends on the magnetic self-impedance of the antenna (measured in Siemens) according to (4):

$$I_M = \frac{V_M}{Z_{M\,self}}; \text{ current moment} = I_M \sqrt{\frac{8}{3}} a \tag{4}$$

The complete duality in Maxwell's equations that is evident once magnetic currents were introduced by O. Heaviside, allow the engineer to translate conventional results of electrically conducting antennas driven by an electric voltage at a gap into the results for magnetically conducting antennas driven by a current flowing in a metal feed loop surrounding the permeable material.

Conventional metal antennas have an Impedance given by the ratio of the applied Voltage, V, to the current that flows in the metal, Ze measured in Ohms. The current, I, can be measured by performing the circulation integral of Ampere's law around the metal wire, that is $$I = \oint \vec{E} \cdot \vec{dl}$$

In the same way, permeable antennas have a dual magnetic impedance, Zm measured in Siemens, given by the ratio of the applied Current, I, in the feed loop to the electromotive force around the permeable rod $$V = \oint \vec{E} \cdot \vec{dl}$$

This is why Zm has the inverse units of Ze. Zm is nothing but the electric admittance, in Siemens, measured by the source driving the current in the permeable antenna's feed loop.

In an ensemble of spheres, the mutual coupling between spheres is represented by the mutual impedance. For electric and magnetic dipoles located on the same x-y plane, all polarized along the z-axis, these are given by Eqs. (5) and (6):

$$Z_{E_{mn}} = \frac{\frac{8}{3} a^2 \frac{\eta_0}{\sqrt{\varepsilon_r(\omega)}} e^{-jkr}}{4\pi r} \left( jk + \frac{1}{r} + \frac{1}{jkr^2} \right) \tag{5}$$

$$Z_{M_{mn}} = \frac{\frac{8}{3}a^2 e^{-jkr}}{\frac{\eta_0}{\sqrt{\varepsilon_r(\omega)}} 4\pi r} \left( jk + \frac{1}{r} + \frac{1}{jkr^2} \right) \quad (6)$$

$Z_{mn}$ is the mutual impedance between the $m^{th}$ and $n^{th}$ sphere. Setting r=a (the radius of the sphere) yields $Z_{mm}$, the self-impedance. (See the Methods section of the incorporated Diaz-Sebastian reference for the details.) With this formulation it is straight-forward to solve self-consistently the problem of the excitation of an ensemble of spheres by any incident field or in particular by one member of the ensemble. Focusing on the simplest case of two spheres, the Voltage at the feed of each antenna depends on the currents on itself and the other antenna, satisfying an equation of the form:

$$V_1 = I_1 Z_{11} + I_2 Z_{12} \quad (7)$$

Thus, under the assumption that the two spheres share the same equatorial plane, the problem of an array of two spheres is represented by a matrix equation of Eq. (8), where all the terms of the Impedance matrix, $\overline{Z}$, are known from equations (5) and (6).

$$\overline{Z} \cdot I = V \rightarrow \begin{pmatrix} Z_{11} & Z_{12} \\ Z_{21} & Z_{22} \end{pmatrix} \begin{pmatrix} I_1 \\ I_2 \end{pmatrix} = \begin{pmatrix} V_1 \\ V_2 \end{pmatrix} \quad (8)$$

To maximize the power transfer from the source to the antenna (and from the antenna to its receiver) we assume that the antennas have been tuned to resonance at the operating frequency either by aid of a matching circuit or the natural resonance of its constitutive materials. This simply means that the self-reactance has been cancelled.

$$Z_{self\_tuned} = Z_{mm} \rightarrow Re(Z_{mm}) \quad (9)$$

To the first order, the input impedance of an electrically small material antenna (as opposed to the idealized perfectly conducting antenna) can be obtained by simply adding in series with the conventional antenna model, the internal impedance of the material. The same argument can be applied to analyze the imperfectly conducting antenna. In the simplest case of a small metal spherical antenna, its external impedance can be approximated by the capacitance of its external near field in series with its radiation resistance. In a lossy dielectric medium the near field capacitance is complex and thus adds extra resistance to the antenna. To resonate (that is to tune) such an antenna the common practice is to add a series inductor such that the series sum of the added inductive reactance and the external capacitive reactance equals zero.

In the same sense a small spherical permeable antenna of radius a, has an external impedance dominated by the magnetic capacitance of its near field. Thus its dual magnetic input impedance is approximately $$Z_m \approx \frac{1}{j\omega C_{m_{ext}}} + R_m = \frac{1}{j\omega \mu_0 \frac{3\pi}{2} a} + R_m \quad (10)$$

Here, Rm is the magnetic dipole's (dual) radiation resistance. Now, assuming the flux inside the permeable sphere is uniform, the internal capacitance can be roughly approximate by a term of the form:

$$C_{m\_int} = \mu_0 \mu_r(\omega) \frac{\pi a^2}{2a} \quad (11)$$

Therefore the total impedance of the material antenna is:

$$Z_m \approx \frac{1}{j\omega \mu_0 \frac{3\pi}{2} a} + R_m + \frac{1}{j\omega \mu_0 \mu_r(\omega) \frac{\pi a^2}{2a}} = \quad (12)$$

$$R_m + \frac{1}{j\omega \mu_0 \frac{\pi}{2} a} \left( \frac{1}{3} + \frac{1}{\mu_r(\omega)} \right)$$

From Eq. (12) a skilled artisan would realize that internal and external capacitances add in series and it is clear that when the real part of the relative permeability of the material, $\mu_r(\omega)$, gets close to the value −3, the reactance is cancelled and the antenna is resonant. At resonance the input impedance of the antenna is purely resistive, consisting of the radiation resistance, the loss resistance of the antenna metal components and the body dielectric, and the loss contributed by the permeable material's imaginary part of the permeability. Because ferromagnetic metal laminates (materials commonly used in the magnetic read-head Industry) have a strong Lorentz-like resonance near 1 GHz this resonance can be tuned to the desired frequency.

In the most general case where the $m^{th}$ sphere in the array is excited and the rest are passive the currents on all antennas are obtained by setting $V_m = 1$, all other $V_{n \neq m} = 0$ and inverting the matrix:

$$\overline{Y} = \overline{Z}^{-1} \therefore I = \overline{Y} V \quad (13)$$

The case of the electric loops is solved similarly and the details of the derivation can be found in the methods section. The final step before solving the case of interest is to define the medium in which the antennas are immersed. As in reference 1, a good approximation below 3 GHz to the FCC accepted model for the human head is the a medium of unity relative permeability and relative permittivity given by the following multi-Debye relaxation model including a DC conductivity of 0.68 S/m (with the frequency written in GHz):

$$\varepsilon_r(f) = \quad (14)$$

$$\varepsilon' - j\varepsilon'' = 8 + \frac{18}{1 + j\frac{f_{GHz}}{0.185}} + \frac{7}{1 + j\frac{f_{GHz}}{9}} + \frac{18}{1 + j\frac{f_{GHz}}{12}} - j\frac{0.68}{0.056 f_{GHz}}$$

The propagation constant and medium impedance appearing in equations (5) and (6) become:

$$k_0 = \frac{2\pi}{\lambda_0} \rightarrow k_{med} = k_0 \sqrt{\varepsilon_r(f)}, \eta_0 = 377 \rightarrow \eta_{med} = \eta_0 / \sqrt{\varepsilon_r(f)} \quad (15)$$

The mutual impedances are, then:

$$Z_{mutual}^{electric} = \frac{\frac{8}{3}a^2 \eta_{med} e^{-jk_{med}r}}{4\pi r}\left(jk_{med} + \frac{1}{r} + \frac{1}{jk_{med}r^2}\right) \text{ electric spheres} \quad (16)$$

$$Z_{mutual}^{magnetic} = \frac{Z_{mutual}^{electric}}{(\eta_{med})^2} \text{ permeable spheres} \quad (17)$$

$$Z_{mutual}^{electric} = \frac{j\eta_{med} k_0 (\pi a^2) e^{-jk_{med}r}}{4r}(k_{med}a)^2\left(1 - \frac{j}{k_{med}r} - \frac{1}{(k_{med}r)^2}\right) \quad (18)$$
electric loops These closed form equations are easy to use and have the pleasing feature that to get the self-impedance we simply set r=a. However for the magnetic dipole case, the self-impedance has an additional series term due to the material properties of the core.

$$Z_{m\,internal} \cong \frac{1}{j\omega\mu_0(\mu(\omega)-1)\frac{\pi a^2}{2a}} \quad (19)$$

So that for the magnetic dipoles the total self-impedance at resonance is given by Eq. (20).

$$Z_{m\,self} = \text{Re}\left[\frac{1}{j\omega\mu_0(\mu(\omega)-1)\frac{\pi a^2}{2a}}\right] + \text{Re}[Z_{mutual}^{magnetic}(r=a)] \quad (20)$$

The first term on the left, the real part of the internal impedance, represents the loss inside the permeable core. This turns out to be inversely proportional to the Heaviside magnetic conductivity of the material $$\left(R_{lossm} = \frac{2a}{\sigma_m \pi a^2}\right)$$

and thus is minimized when the material has a very large initial permeability (500 in our example) and when the operating frequency is chosen as the resonant frequency of the material. This choice also maximizes the input impedance.

Having defined all the relevant parameters, the current induced on a second antenna as a function of the current in the source antenna and the separation between them can be calculated. For example, assuming there are two spheres (or loops) each of radius a=10 μm, separated from each other by a distance d, we let the distance d range from 5 mm to 4 cm in steps of 5 millimeters. The results, plotted as the ratio of the induced current to the source current, are shown as points in FIG. 5. The advantage of the operational magnetic dipole antenna by about 4 orders of magnitude is startling. This corresponds to an 8 order of magnitude increase in power transmission that is, +80 dB gain over the conventional alternatives.

To emphasize that the nature of the receiving antenna is as important as that of the transmitting antenna, FIG. 5 also displays, as curves, the ratio of the principal field at the distance r=d to the maximum value of that field at the surface of the antenna r=a.

$$E_\theta(r) = \frac{\eta_0}{\sqrt{\varepsilon_r(\omega)}}\frac{I_e\sqrt{\frac{8}{3}}a}{4\pi r}e^{-jkr}\left(jk + \frac{1}{r} + \frac{1}{jkr^2}\right)\sin\theta \text{ electric sphere} \quad (21)$$

$$H_\theta(r) = \frac{\sqrt{\varepsilon_r(\omega)}}{\eta_0}\frac{I_m\sqrt{\frac{8}{3}}a}{4\pi r}e^{-jkr}\left(jk + \frac{1}{r} + \frac{1}{jkr^2}\right)\sin\theta \text{ magnetic sphere} \quad (22)$$

$$H_\theta(r) = \frac{-(ka)^2 I_e}{4r}e^{-jkr}\left(1 + \frac{1}{jkr} - \frac{1}{(kr)^2}\right)\sin\theta \text{ electric loop} \quad (23)$$

By examining this graph, a skilled artisan appreciates a significant difference in the behavior of the magnetic antenna. All the normalized fields lie on top of each other and 4 centimeters away the normalized field has dropped down by a factor of $3\times10^{-19}$ compared to the field at the surface: −190 dB down. Electric dipole to electric dipole mutual coupling follows this same trend being slightly larger by a factor of 3, while the electric loop to electric loop coupling follows the same trend but stronger by about a factor of 10. The magnetic dipole coupling exceeds the field ratio by almost 5 orders of magnitude.

Figure 6B:
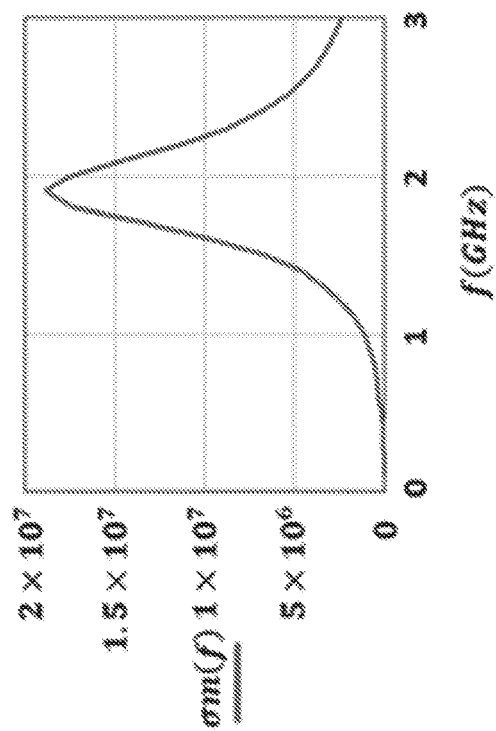
FIGS. 6A, 6B illustrate permeability characteristic and Heaviside magnetic conductivity, respectively, of a typical high-frequency ferromagnetic material.
Figure 6A:
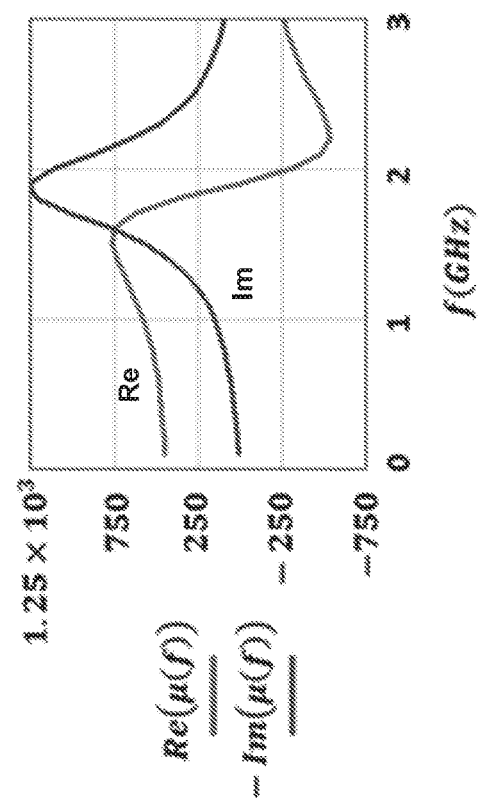

The materials used, according to the idea of the invention, for a typical magnetic dipole antenna have the permeability parameters shown in FIGS. 6A, 6B. These magnetic materials already exist and having a high $\mu_{initial}$ is an important factor which will result in having a strong magnetic conductivity. The efficiency of the magnetic dipole antennas are much higher than the other two alternatives which are the electric dipole antenna and the electric loop antenna because the magnetic material used for these antennas changes both the dipole moment and the input impedance. To illustrate the importance and role of the high permeability material, two more data points were added to FIG. 5 at the distance of 4 cm showing that for $\mu_{initial}$=50 and $\mu_{initial}$=200 the advantage is not as significant as the $\mu_{initial}$=450.

The plot of the induced current in the electric loop, shown in FIG. 5, illustrates the normalized induced current in the electric loop at 4 cm (far enough to get to the surface of the head from almost everywhere inside the brain) is stronger than the normalized induced current in the electric dipole and, at $3\times10^{-9}$, it is about an order of magnitude stronger than the normalized field. But the current induced in the magnetic dipole is $2\times10^{-5}$, almost five orders of magnitude larger than the field ratio.

The behavior of an antenna depends on the quality or the "Q" of its resonance and the signal that the antenna receives is directly proportional to its ability to resonate at the receiving frequency and the Q is inversely proportional to the damping. So if we have a strongly damped antenna we almost respond one to one and the response is a direct proportion to the field strength. Electric dipoles at this size are strongly damped because of the near field direct loss in the body, and at this size electric copper loops are also very much damped because of the required large current that dissipates a large amount of energy into their own conductivity. Therefore the response of electric dipoles and electric loops follow the field. But since the magnetic dipole has low body currents and low metal currents they are much less damped. The excess loss of the metal antennas will also result in a reduced receiving and transmitting cross sections when compared to the more efficient magnetic dipoles.

The magnetic dipole antenna is fed by a loop but the effect of the permeable core is to change the character of the antenna from the short circuit of the electric loop, which has a high current, to an antenna that tends to an open circuit at resonance which as mentioned before is typical of dipoles, since dipoles are open circuits. Therefore its damping is dominated not by the copper loss but by the constitutive properties of its core. The ferromagnetic metals developed for the magnetic read-head industry on purpose combine high permeability with low damping and this is evidenced in the Lorentz line shape of their frequency dependent permeability; they are by design high Q materials.

The discussion and results above, especially the +80 dB gain in power transfer efficiency over electric dipoles and electric loops, prove the feasibility of use of magnetic dipole antennas for neuron-by-neuron RF telemetry inside lossy dielectric media (such as bodily/neural tissue).

To verify the correctness of the chosen approach, an additional set of calculations was performed in which we set the surrounding medium to free space. Such change of surrounding medium removes the advantage of the magnetic dipoles over the electric dipoles and loops and, indeed, all of the antenna types showed the exact same induced current.

From the presented discussion it is recognized that the use of magnetic materials with high permeability and high resonant frequency for constructing the magnetic dipole elements of the present invention is preferred. Given the small size of the antennas involved and the level of maturity of magnetic read-head industry it can be anticipated that the development and production cost of these materials would not be an obstacle to their use. Magnetic read-head industry materials include multi-layers of "Permalloy" or other alloys with transition metals (such as FeCoHf thin film) that have permeability values in the hundreds and resonance frequencies as high as a few GHz. The magnetic properties of these materials can further be controlled by patterning their layers to control the formation of domains and alter the magnetic anisotropy. Typical dimensions for these design features are in the 0.2 μm range, which is fully compatible with an antenna structure of the assumed 10 μm size.

It can be seen, therefore, that the use of coupled magnetic dipole antennas (FIGS. 3A, 3B) as microscopic links in an in-vivo telemetry system provides a solution to the tissue damage problem caused by electric dipole antennas through SAR deposition and the electric loop antennas through heat conduction. If the head is modeled as a sphere having a radius of several centimeters, communication between a first transmitting microscopic antenna disposed anywhere inside the brain and an identical second antenna one used as a repeater node located just under the skull would potentially result in the +80 dB in gain seen in FIG. 5 as compared to conventional antenna alternatives.

Embodiments of In-Vivo Neuronal Telemetry According to an Idea of the Invention.

Figures 7A, 7B:
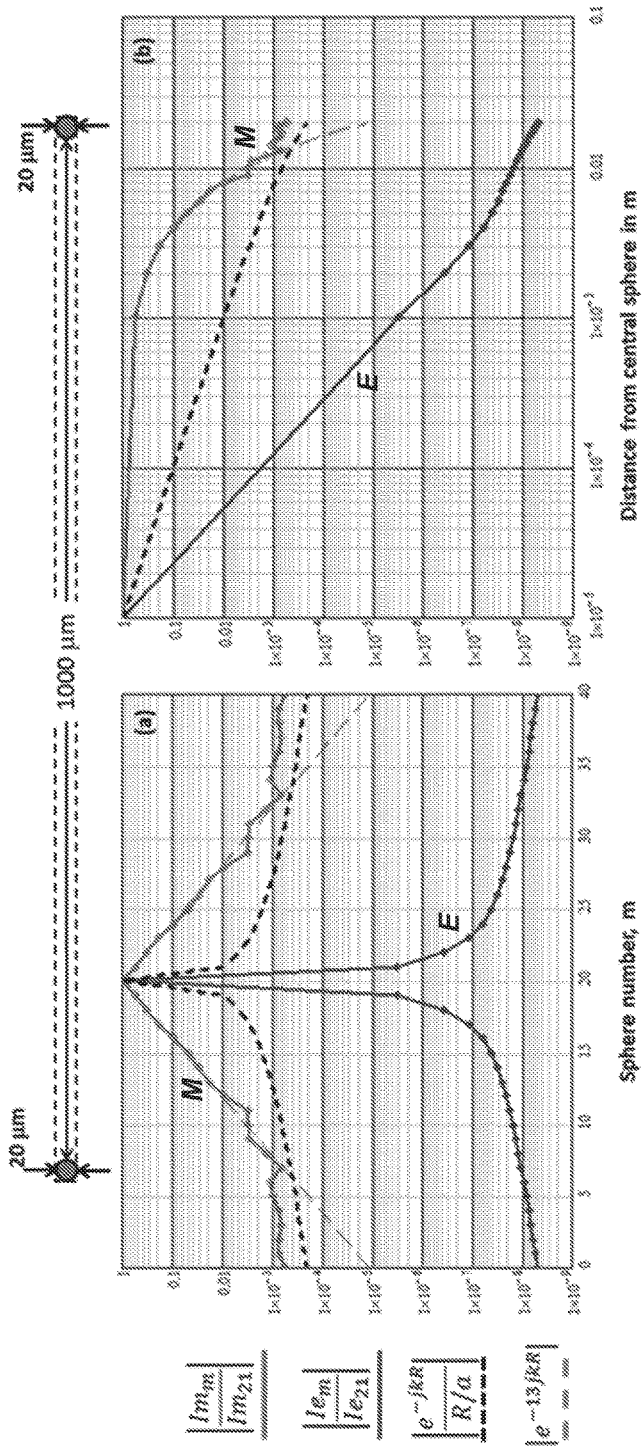
FIGS. 7A, 7B provide plots illustrating propagation of an RF signal along a chain of microsized antennae (electric dipoles in comparison with magnetic dipoles) tuned resonantly to a chosen RF.

Here, elements of an embodiment of an antenna structured according to the idea of the invention are assumed to be spherical sized to operate, in one example, inside the brain and, therefore, have a radius of 10 microns (or a similar value, for example, 20 microns). Defining a distance separating immediately neighboring individual magnetic dipole antenna elements as one-quarter wavelength of the RF frequency at which the array of magnetic dipoles transmits reveals that for micro-sized antennae at 2 GHz such distance is about 5 mm. Calculating the propagation of a signal along a chain of tuned to resonance 20 micron diameter antennae the immediately neighboring of which are separated by 1 mm distance, and with the central antenna element transmitting, the recovery of power transmitted by magnetic dipoles is +50 dB compared to the power transmitted by electric dipoles (as seen from the comparison of curves E, M of FIGS. 7A, 7B).

The optimization of such operation may require the dipoles that have three possible states: a) resonant connected to its internal source, b) resonant but source terminals shorted, c) non-resonant. The array of dipoles has to be governed with an external command (delivered from outside the bodily tissue in which the array is embedded) configured to trigger a change of state of any particular dipole. In one possible configuration, the resonant node of the array is connected to its internal source and acts as the source magnetic dipole element for the whole array.

Figure 8:
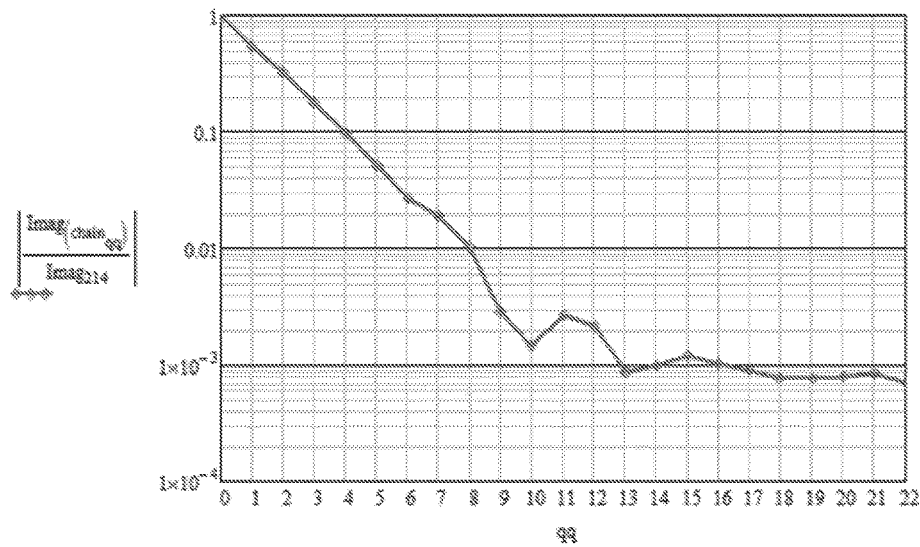
FIG. 8 is a plot illustrating efficiency of RF signal propagation along an ad-hoc path through an array of magnetic dipoles of FIG. 9.
Figure 9:
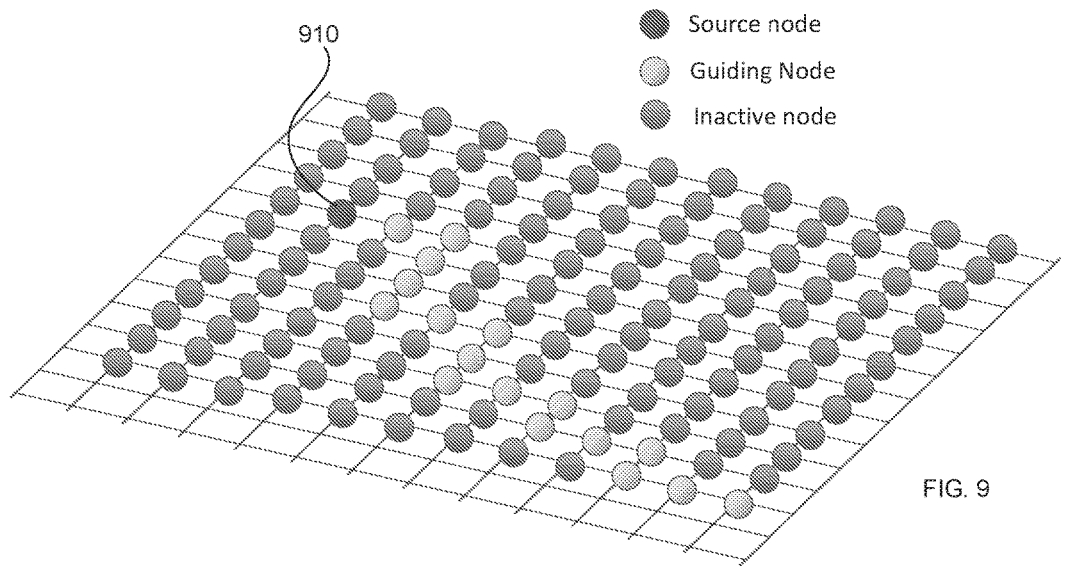
FIG. 9 is a schematic illustration of a two-dimensional array of magnetic dipoles configured as a transmission line according to an embodiment of the invention.

In one embodiment, only the short-circuited resonant nodes act to guide the signal wave. (Were other resonant nodes allowed to remain connected to their internal sources they would absorb the wave instead of guiding it.) The non-resonant nodes cannot respond to the wave. Under these conditions, the signal from the source dipole should be transmissible to the nearest point of the surface of the head through an array of the magnetic dipole elements (whether linear or 1D, 2D, or 3D). The energy is guided along the ad hoc path with the same efficiency as if such path were an isolated straight line, see FIG. 8. An example of a 2D array of magnetic dipoles the individual elements of which are separated by a distance defining near-field interaction between them is shown in FIG. 9, with the element 910 indicated to be a source for the whole array.

Macroscopic Embodiment of Wireless Transmission Line.

Figure 10:
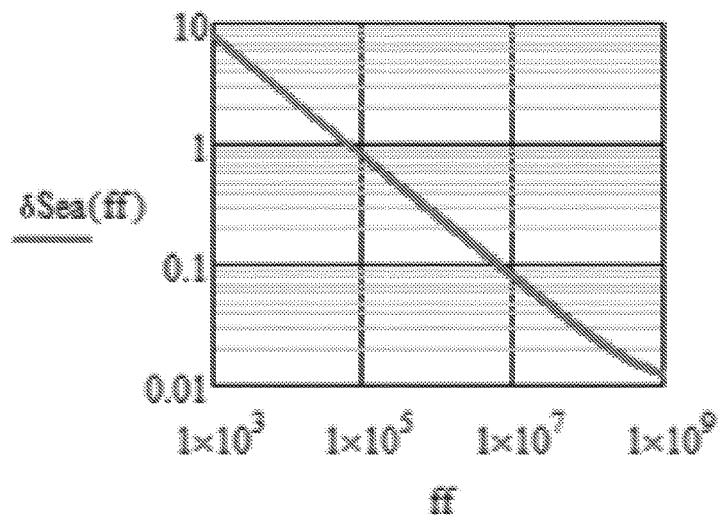
FIGS. 10, 11, 12, and 13 are plots showing operational parameters of RF signal propagation along passive identified arrays structured according to alternative implementations.

FIG. 10 provides an illustration facilitating designs of the transmission line in sea-water or ice-water medium. The dielectric properties of such media are approximately:

$$\varepsilon_{r-ice} \cong 4.9 + \frac{105}{1 + j\frac{f}{3 \text{ KHz}}} \quad (24)$$

$$\varepsilon_{r-sea} \cong 4.9 + \frac{75.1}{1 + j\frac{f}{16.8 \text{ GHz}}} - j\frac{4}{2\pi f \varepsilon_0}$$

With an assumption of an acceptable −85 dB of transmission loss of a signal, the thickness of a medium through which the transmission of radiation from a single antenna would be successful is approximately 10 skin depths which, at 1 GHz and for δsea=1 cm, is about 10 cm of water. A large antenna with 30 dB directive gain would only buy us three more skin depths. At 10 MHz 10 skin depths would take us to 1 meter away but the only reasonably sized antenna is now a dipole so no extra directive gain can help us. At 1 KHz the skin depth is 8 meters and 10 skin depth values is about 80 meters.

Figure 11:
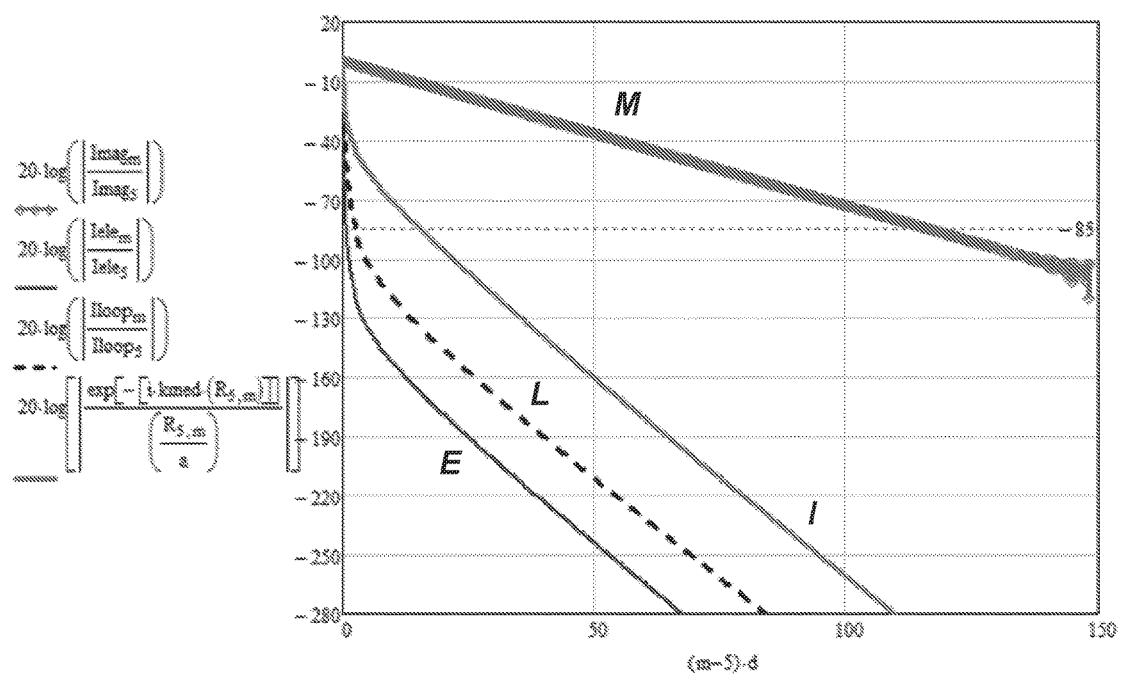

In comparison, FIG. 11 illustrates the performance of an array of 2-inch diameter dipoles in sea water. The dipoles are spaced at 1 foot center to center distance and operate with a 3 KHz carrier (communication channel of about 300 bps). Curve L corresponds to loop antennas, curve E represents electric dipoles (configured as a chain or individually), curve M corresponds to magnetic dipoles (made with $Co_2Z$ hexaferrite, unaligned, as permeable core). Curve I represents the exponent $e^{-jkr}/r$. it is readily apparent that, for the −85 dB loss threshold, the transfer of energy along the array of magnetic dipoles can reach 115 m. It is notable that the magnetic dipoles are passive: they form a virtual transmission line.

Figure 12:
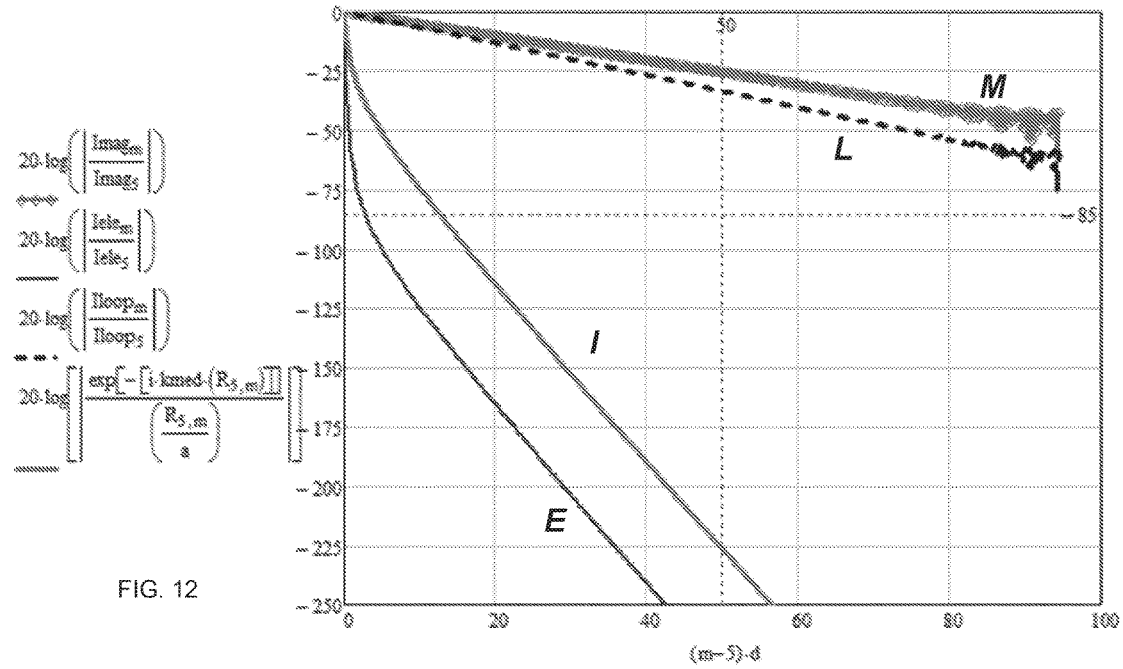

In comparison with FIG. 11, FIG. 12 illustrates that, while loop antennae can also couple signal to one another, they have to be a lot bigger than magnetic dipoles with corresponding and comparable performance. For instance, curve L illustrates the performance of 8 inch diameter loop antennas separated, center-to-center, by a 1 foot distance tend to guide a 10 KHz signal. Curve E illustrates electric dipoles (configured as a chain or individually), while curve M corresponds to magnetic dipoles (that use Co2Z hexaferrite, unaligned, as permeable cores). Curve I represents the exponent $e^{-jkr}/r$.

Figure 13:
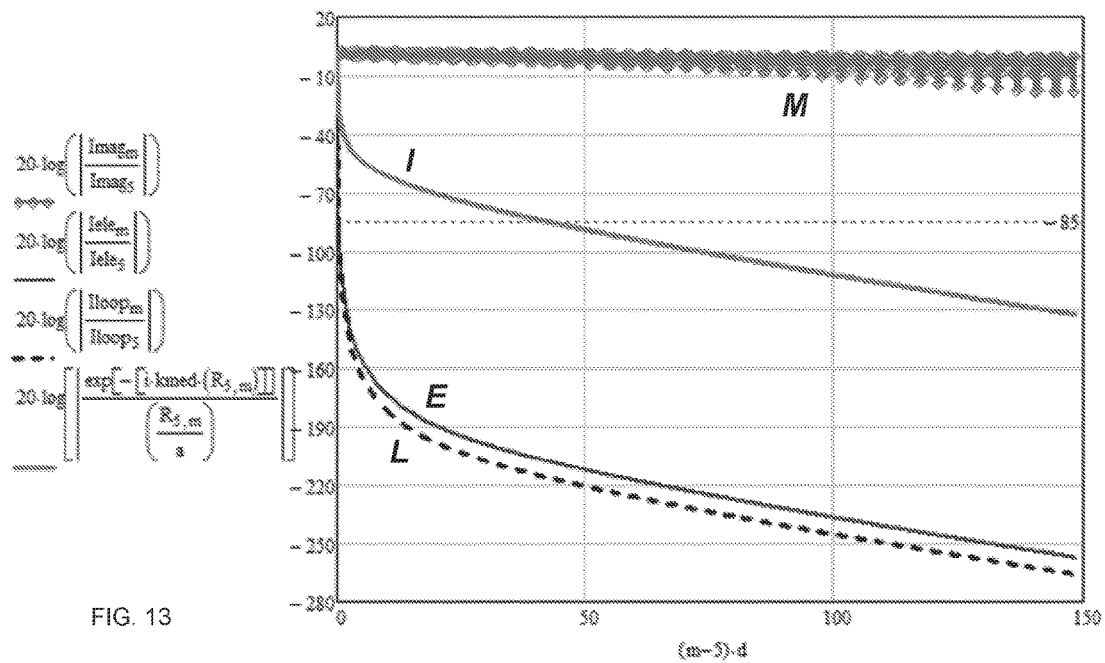

As follows from FIG. 13, providing plots for operational performance of the arrays of FIG. 13 at 100 Hz. Notably, for really low data rates, using a 100 Hz carrier, an array of 1 inch diameter magnetic spheres 1 foot apart constitute an almost lossless transmission line. Shown are the results of simulating of a chain of 500 spheres reaching out, in terms of transmission of a signal, to 150 m What has been discussed, therefore, is transmission lines made of magnetically-permeable materials which, although conventionally considered lossy, are employed as true magnetic dipoles in a conducting/lossy environment. While such lines may be configured to employ a structure of the Yagi-Uda array antenna, they are devoid of metallic elements. With the use of this structural principle, the lines create a high directivity beam(s) by coupling the power from one source dipole antenna into a chance of electromagnetically-coupled passive antenna elements. Such coupling is effectuated through the near-field interaction and is efficient even in a conductive environment.

In particular, the use of the idea of the invention produces a wireless power transmission line configured to operate in a conductive medium. Such line includes a source magnetic dipole element configured to operate at a chosen frequency; and an array of magnetic dipole elements that are separated from one another by a distance defining near-field interaction between immediately neighboring magnetic dipole elements of the array. The outmost element of the array is separated from the source by such distance as well. The array of magnetic dipole elements may include at least one of a one dimensional array, two-dimensional array and a three-dimensional array. The transmission line can be complemented with electronic circuitry configured to tune at least one of a configuration of elements of the transmission line and the chosen frequency and, in a specific case, the electronic circuitry may be configured to tune the chosen frequency. In a specific implementation, the magnetic dipole elements of the array include spherical elements with diameters not exceeding 1.5 inches and/or elements having a longest dimension that does not exceed one half wavelength in a conducting medium in which the transmission line is embedded.

Another implementation of the idea of the invention results in a method for wireless transmission of power in a conductive environment. Such method includes a step of causing a source magnetic dipole element radiate energy by emitting a signal at a chosen frequency; a step of passively transferring said signal between said source magnetic dipole element and an outer element at a first end of an array of magnetic dipole elements, which outer element is separated from the source magnetic dipole element by a distance defining a near-field interaction between these two. A method further includes a step of passively transferring the signal from the outer element to an element at a second end of the array only via near-field interactions between elements of the array. Alternatively or in addition, the method includes a step of disposing the source magnetic dipole element and the array in the conductive medium and/or disposing the array in the conductive medium such that each of elements of the array are embedded in the conductive medium. In one specific case, the array is disposed under the surface of a sea Furthermore, the implementation of the idea of the invention results in a neuronal radio-frequency (RF) telemetry system. Such system includes a microscopically-sized neuronal sensor tuned to a resonance at a chosen radio-frequency (RF); an electronic circuitry operably connected to said sensor. The system further includes a passive array of microscopically-sized neuronal transmitter elements separated from one another by a distance that defines a near-field interaction between immediately neighboring elements of such passive array. An outmost transmitter element of the array is separated from the neuronal sensor by a distance that defines a near-field interaction between the sensor and the outmost element at the chosen radio-frequency. The system further includes a receiver in RF communication at least with the outmost transmitter element. In one embodiment, the neuronal sensor includes a source magnetic dipole element and said transmitter elements include passive magnetic dipole elements. The passive array may be configured as at least one of a one dimensional array, two-dimensional array and a three-dimensional array, while the telemetry system can be complemented with electronic circuitry configured to tune at least one of (i) a configuration of elements of the telemetry system and (ii) the chosen frequency. The microscopically-sized neuronal transmitter elements may include antenna elements having a longest dimension not exceeding one half wavelength of an RF wave in the surrounding medium It is appreciated that control of operation of an embodiment of the invention may require a processor controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the disclosed inventive concepts, which may be combined in ways not listed above. Accordingly, the invention should not be viewed as being limited to the disclosed embodiment(s).

What is claimed is:

1. A neuronal radio-frequency (RF) telemetry system comprising:

a microscopically-sized neuronal sensor tuned to a resonance at a chosen radio-frequency;

an electronic circuitry operably connected to said neuronal sensor, a passive array of microscopically-sized neuronal transmitter elements separated from one another by a distance that defines near-field interaction between immediately neighboring neuronal transmitter elements of the passive array, wherein an outmost transmitter element of said array is separated from the neuronal sensor by the distance, and a receiver in RF communication at least with the outmost transmitter element.

2. A telemetry system according to claim 1, wherein said neuronal sensor includes a source magnetic dipole element and said transmitter elements from the passive array include passive magnetic dipole elements.

3. A telemetry system according to claim 1, wherein the passive array includes at least one of a one-dimensional array, a two-dimensional array, and a three-dimensional array.

4. A telemetry system according to claim 1, further comprising electronic circuitry configured to tune at least one of (i) a configuration of elements of said transmission line and (ii) the chosen frequency.

5. A telemetry system according to claim 1, wherein said microscopically-sized neuronal transmitter elements include antenna elements having a longest dimension that does not exceed one half wavelength corresponding to said chosen frequency in a medium surrounding the telemetry system.

6. A telemetry system according to claim 1, configured to operate in a conductive medium.

\* \* \* \* \*